United States Patent
Isbert et al.

(10) Patent No.: US 6,741,411 B2
(45) Date of Patent: May 25, 2004

(54) CHANGEABLE PROCESS WINDOW

(75) Inventors: Karl Isbert, Krefeld (DE); Lutz Spauschus, Kerken (DE); Ulrich Heesen, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 33 days.

(21) Appl. No.: 10/325,377

(22) Filed: Dec. 20, 2002

(65) Prior Publication Data

US 2003/0133210 A1 Jul. 17, 2003

(30) Foreign Application Priority Data

Jan. 17, 2002 (DE) .......................... 102 01 541

(51) Int. Cl.[7] .......................... G02B 27/00; G02B 5/00; G02B 7/00

(52) U.S. Cl. .................. 359/894; 220/663; 116/276; 73/330; 73/334

(58) Field of Search ................ 359/894, 895, 359/509, 440; 220/663; 116/276; 73/325, 330, 334; 422/55

(56) References Cited

U.S. PATENT DOCUMENTS 3,578,407 A * 5/1971 Arnold ...................... 422/310
4,738,064 A * 4/1988 Aarts ........................ 52/204.5
4,807,474 A * 2/1989 Foster .......................... 73/331
5,120,129 A 6/1992 Farquharson et al. ....... 356/246
5,383,338 A * 1/1995 Bowsky ........................ 62/125

FOREIGN PATENT DOCUMENTS

| DE | 2 312 515 | 9/1974 | ............. B01J/3/00 |
| DE | 30 10 278 | 10/1980 | ............ F17C/13/06 |
| DE | 33 05 982 A1 | 8/1984 | .......... G01N/21/03 |
| DE | 94 03 540 | 5/1994 | .......... G01N/21/01 |
| EP | 0 652 429 A2 | 5/2000 | .......... G01N/21/47 |
| WO | WO 00/58711 | 10/2000 | ............ G01N/2/03 |

OTHER PUBLICATIONS

Patent Abstracts of Japan, JP 03024372, Feb. 1, 1991, "Sealing Structure of Through Portion High Pressure Gas Device", NKK Corp/Nakanishi Kazuo.

* cited by examiner

Primary Examiner—Drew Dunn
Assistant Examiner—Leo Boutsikaris
(74) Attorney, Agent, or Firm—Norris McLaughlin & Marcus

(57) ABSTRACT

A process window unit for the spectroscopic study of process mixtures The process window is comprised of a window frame for holding a window, a screw cylinder, with a radiation passage in its core and an external thread for screwing the screw cylinder into the window frame as well as an elastic seal between the window and the screw cylinder, the window being designed with a conically tapering profile on the process side opposite the screw cylinder.

6 Claims, 3 Drawing Sheets

CHANGEABLE PROCESS WINDOW

The invention relates to a changeable pressure-tight process window unit for the optically spectroscopic study of pipelines or apparatus through which products flow.

BACKGROUND OF THE INVENTION

DE 4 414 975 A1 describes a device for the spectroscopic analysis of process mixtures, whose main component is a measurement crystal which is immersed in the process space and which is arranged below two conically profiled process windows for the input and output of measurement radiation. In this case, the windows are arranged in such a way that the cone diameter widens towards the apparatus interior side in order, when operating under high pressure, to obtain a self-sealing barrier for the process mixture in the reactor interior after a break of the measurement crystal. The use of adhesives for the process windows mentioned in DE 4 414 975 A1 is also proposed.

It is an object of the invention to develop an improved process window unit which, on the one hand, can be fitted pressure-tightly on a container or a pipeline and, on the other hand, can be rapidly installed and removed for cleaning and monitoring purposes.

SUMMARY OF THE INVENTION

The object is achieved according to the invention by a process window unit comprised of a window frame for holding a window, a screw cylinder with a radiation passage in its core and an external thread for screwing the screw cylinder into the window frame, the window frame having a complementary internal thread, and an elastic seal between the window and the screw cylinder, wherein the window is designed with a conically tapering profile on the process side opposite the screw cylinder. That is to say, the window is conically tapered away from the screw cylinder.

In a preferred embodiment, the process window unit has an additional seal above the thread of the screw cylinder, between the screw cylinder and the window frame.

The fastening of the process window unit to the container or pipeline is particularly advantageously carried out by means of a clamp-ring screw connection, which is fastened to the pipeline or the container, in particular releasably. The clamp ring of the clamp-ring screw connection is designed conically narrowed downwards, and it is pressed into the seal seat of the screw connection with the aid of a union nut on the screw connection, in such a way in that its inner face bears with a force-fit on the outer face of the screw cylinder. The process window unit, as an insert in the clamp-ring screw connection, can easily be removed from the pipeline or the process container, by removing the union nut and withdrawing the process window unit.

As an alternative to the clamp-ring screw connection, a second external thread may be fitted on the outer diameter of the screw cylinder, with the aid of which the process window unit can be screwed directly into an opening in the pipeline wall having a complementary internal thread. In this case, further ring seals are provided below the second external thread in the screw cylinder, i.e., disposed on said screw cylinder to enter said opening in advance of said second external thread, in order to seal the connection between the screw cylinder and the opening in the pipeline wall.

The process window unit permits, for example, inline measurement on any pipelines or reaction containers through which products flow. Optionally, the process window unit may also be fitted on a separable pipeline flange. Preferably, in particular for spectroscopic irradiation measurements, an arrangement is selected in which two process window units according to the invention are fitted opposite each other in a pipeline or a container.

The seals may be formed from known materials in accordance the requirements of the respective process in which they are to be used. Such materials include, for example, polytetrafluoroethylene (PTFE), Kalrez, (per fluoroelastomer) Viton Vinylidenfluorid hexafluoropropylene copolymerisate or at higher extreme temperatures and extreme pressure, Helicoflex rings may be used. For the clamp-ring screw connection, commercially available screw connections with standardized internal diameter may be used, to which the screw cylinder is optionally matched in terms of its external diameter.

For the mechanical parts of the process window which come into contact with product, the usual materials, such as stainless steel, possibly tantalum, Hastelloy™ nickel-based alloy, or even polyvinyl difluoride (PVDF)—may be suitable. The optical parts, i.e., the windows, may be formed of the usual optical materials sapphire, glass, quartz glass, transparent plastic and the like.

BRIEF DESCRIPTION OF THE DRAWINGS

The invention will be explained in more detail below by way of example and with reference to the figures, in which.

EXAMPLES

Figure 1:
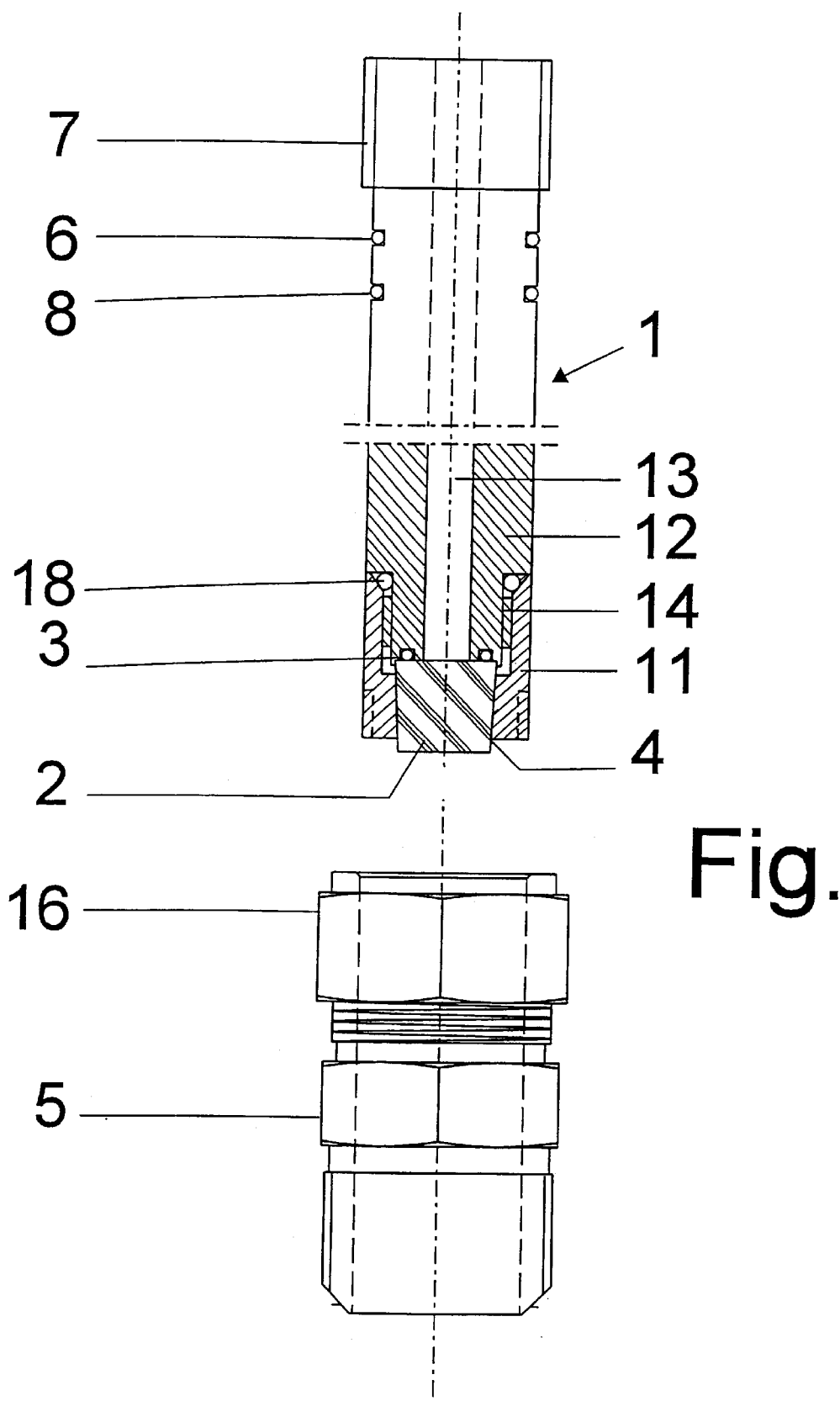
FIG. 1 shows a process window unit according to the invention in cross section, separated from the clamp-ring screw connection

FIG. 1 shows in the upper part a cross section through a process window unit 1 with the conical window 2, which is put into the window frame 11. The window 2 has a standard profile with the standard slope of 1:10. The window 2 is held firmly in the window frame by means of the screw cylinder 12, whose external thread 14 engages in the internal thread of the window frame 11. A ring seal 3 of elastic sealing material ensures stress-free fastening of the window 2. This construction permits uniform pressure transmission through the seal 3 onto the window 2. The cone profile of the window 2 bears the load over the entire area. The ring gaps 4 which are usual in other window designs, and in which for example perturbing old measurement-solution residues can become lodged, are hence absent.

Figure 2:
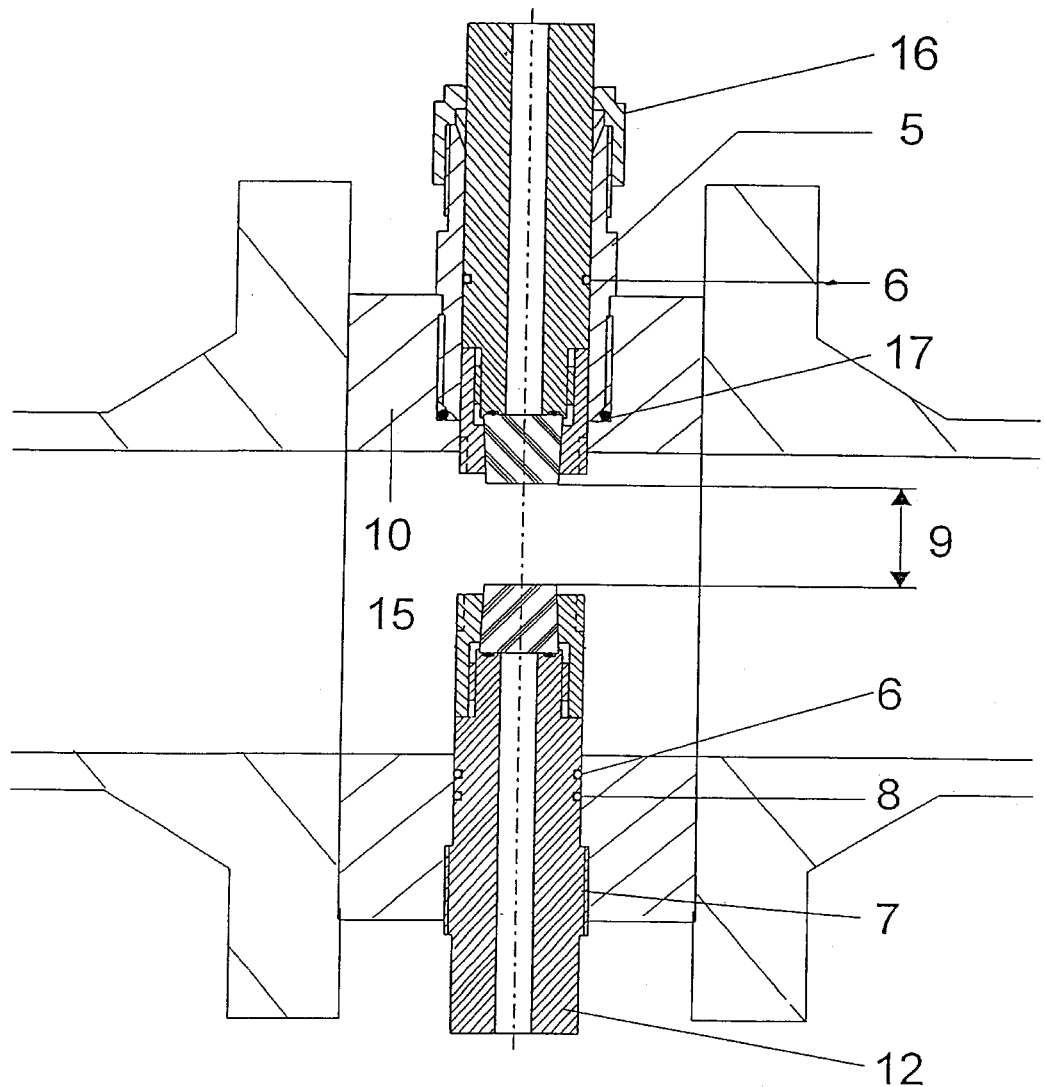
FIG. 2 shows a cross section of a pipeline with two oppositely arranged process window units, the upper of which is fastened by means of a clamp-ring screw connection 5 and the lower of which is fastened by means of a threaded screw connection directly into a flange piece 10 of the pipeline.

The process window unit 1 is fitted into the clamp-ring screw connection 5 (see FIG. 2 above) and is fixed by means of the union nut 16 of the clamp-ring screw connection 5. The lower part of the clamp-ring screw connection 5 is screwed into a flange piece 10 of a pipeline and is sealed against the process space 15 by means of a sealing ring 17.

Figure 3:
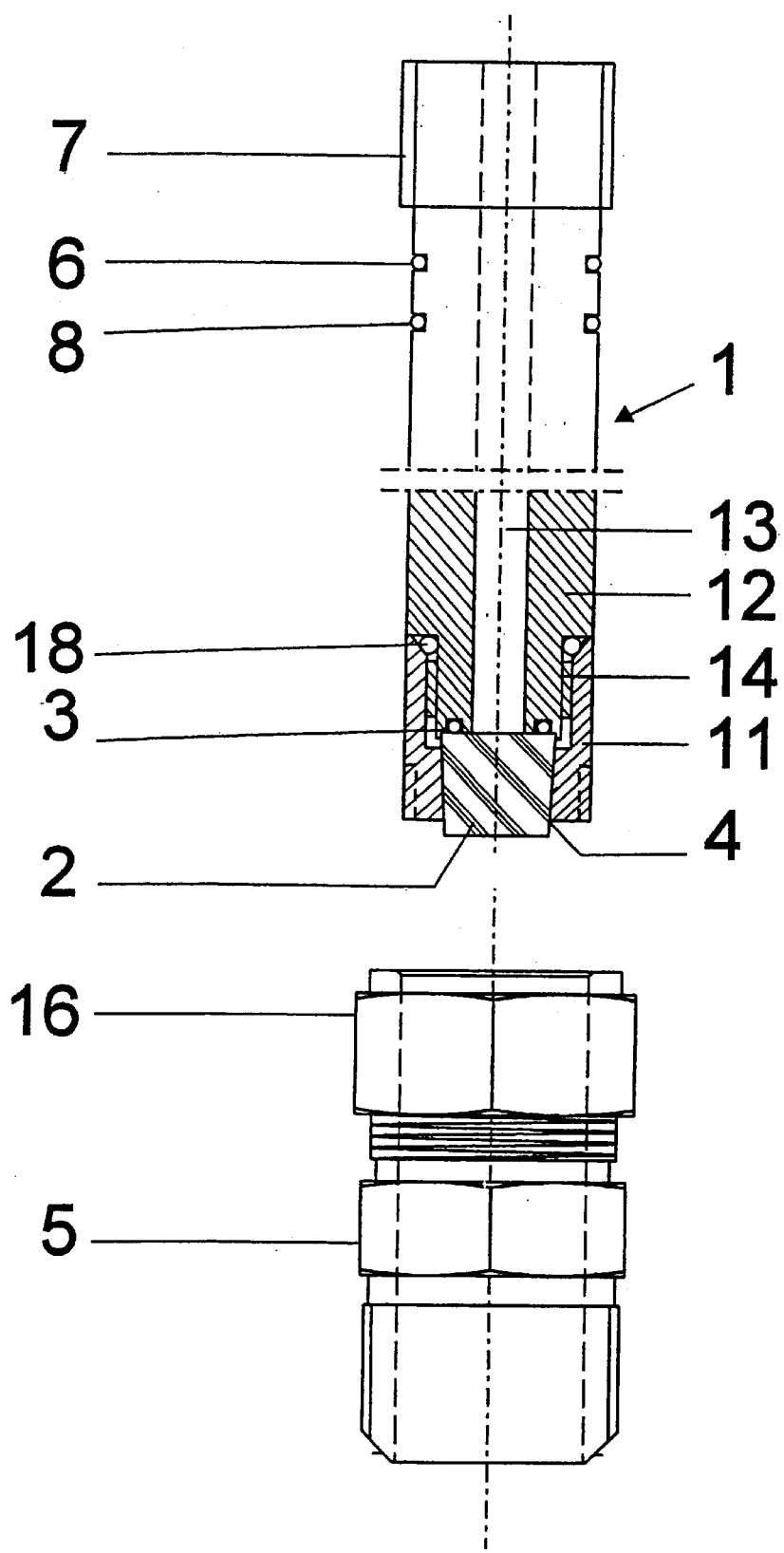
FIG. 3 shows a process window similar to FIG. 1 with an additional sealing-ring.

The upper part of FIG. 1 shows an alternative to the screw connection by means of a clamp ring 5. In this case, the screw cylinder 12 has at its upper end an external thread 7 as well as further sealing rings 6 and 8 in ring grooves. A process window unit configured in such a way is screwed into the internal thread of the pipe flange 10. With this design, two opposite optical windows 2 can be mounted at any desired mutual separation, a reproducible optical layer thickness 9 being obtained. In the alternative process window according to FIG. 3 there is an additional sealing-ring 18a located above the thread 14.

With the aid of such a process-window arrangement, the inline measurement on pipelines through which products flow is simplified. The flange piece 10 shown in FIG. 2 may, for example, be built directly into a process line or a process branch line.

We claim:

1. A process window unit for the spectroscopic study of process mixtures in pipelines or containers, comprised of a window frame for holding a window, a screw cylinder with a radiation passage in its core and an external thread for screwing the screw cylinder into the window frame, the window frame having a complementary internal thread, as well as an elastic seal between the window and the screw cylinder, wherein the window is conically tapered away from the screw cylinder.

2. The process window unit of claim 1, wherein a further seal is provided, between the screw cylinder and the window frame.

3. The process window unit of claim 1, wherein the process window unit is adapted for connection to a pipeline or container by a clamp-ring screw connector, which is fastened to the pipeline or the container.

4. The process window unit of claim 3, wherein said connection is a releasable connection.

5. The process window unit of claim 1, wherein a second external thread is fitted on the outer diameter of the screw cylinder and is adapted to be screwed directly into a complementary internal thread of an opening in a pipeline or container wall, with ring seals disposed on said screw cylinder to enter said opening in advance of said second external thread.

6. An optical process window system, comprising two process window units of claim 1, arranged opposite one another in a pipeline or a container.

* * * * *